(12) United States Patent
Borgos et al.

(10) Patent No.: US 11,806,494 B2
(45) Date of Patent: Nov. 7, 2023

(54) SYSTEMS AND METHODS FOR THE TREATMENT OF PELVIC DISORDERS INCLUDING MAGNETIC PARTICULATES

(71) Applicant: Boston Scientific Scimed, Inc., Maple Grove, MN (US)

(72) Inventors: Natalie Ann Borgos, Lino Lakes, MN (US); Tania M. Schroeder, Hastings, MN (US); David J. Yonce, Fridley, MN (US); Robert E. Lund, Saint Michael, MN (US); Suranajan Roychowdhury, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 267 days.

(21) Appl. No.: 17/301,831

(22) Filed: Apr. 15, 2021

(65) Prior Publication Data
US 2021/0299421 A1    Sep. 30, 2021

Related U.S. Application Data

(63) Continuation of application No. 16/103,390, filed on Aug. 14, 2018, now Pat. No. 11,007,357, which is a
(Continued)

(51) Int. Cl.
*A61F 5/41*    (2006.01)
*A61M 35/00*   (2006.01)

(52) U.S. Cl.
CPC ............ *A61M 35/003* (2013.01); *A61F 5/41* (2013.01); *A61F 2005/411* (2013.01); *A61F 2005/418* (2013.01)

(58) Field of Classification Search
CPC .................................................. A61K 9/5094
See application file for complete search history.

(56) References Cited

U.S. PATENT DOCUMENTS

| | | | |
|---|---|---|---|
| 2,036,550 A | 4/1936 | Stevens et al. | |
| 4,005,699 A | 2/1977 | Bucalo et al. | |
| (Continued) | | | |

FOREIGN PATENT DOCUMENTS

| | | |
|---|---|---|
| EP | 2036550 A1 | 3/2009 |
| WO | 2004000369 A2 | 12/2003 |
| WO | 2009120879 A1 | 10/2009 |

OTHER PUBLICATIONS

Arshady, et al., "Albumin microspheres and microcapsules: Methodology of manufacturing techniques", Journal of Controlled Release, vol. 14, Issue 2, Oct. 1990, pp. 111-131.
(Continued)

*Primary Examiner* — Thaddeus B Cox
(74) *Attorney, Agent, or Firm* — Brake Hughes Bellermann LLP

(57) ABSTRACT

Systems and methods of localizing or delivery cells, biologics and/or drugs to a specific target area to treat pelvic health disorders are provided. A treatment composition including cells, biologics and/or drugs are associated with magnetic particulates, and the positioning of these materials is facilitated through use of a magnetic field-generating device that is configured to be placed on or into a pelvic anatomical structure. Certain embodiments directed to the treatment of ED in male patients can include a cell based therapy system.

11 Claims, 9 Drawing Sheets

Related U.S. Application Data continuation of application No. 15/613,664, filed on Jun. 5, 2017, now Pat. No. 10,076,647, which is a continuation of application No. 13/205,039, filed on Aug. 8, 2011, now Pat. No. 9,669,200.

(60) Provisional application No. 61/371,609, filed on Aug. 6, 2010, provisional application No. 61/371,232, filed on Aug. 6, 2010.

(56) References Cited

U.S. PATENT DOCUMENTS

| | | | |
|---|---|---|---|
| 4,279,256 A * | 7/1981 | Bucalo | A61N 1/36007 607/71 |
| 4,967,738 A | 11/1990 | March et al. | |
| 5,823,191 A | 10/1998 | Cho | |
| 6,050,959 A | 4/2000 | Card | |
| 6,348,033 B1 | 2/2002 | Catlett et al. | |
| 6,541,039 B1 | 4/2003 | Lesniak et al. | |
| 6,589,159 B2 | 7/2003 | Paturu et al. | |
| 6,866,842 B1 | 3/2005 | Chancellor et al. | |
| 6,945,250 B2 | 9/2005 | Shapiro et al. | |
| 6,979,466 B2 | 12/2005 | Esniak et al. | |
| 7,115,417 B1 | 10/2006 | Capelli et al. | |
| 7,553,662 B2 | 6/2009 | El Haj et al. | |
| 7,625,562 B2 | 12/2009 | El et al. | |
| 7,959,550 B2 | 6/2011 | Aniado et al. | |
| 9,669,200 B2 | 6/2017 | Borgos et al. | |
| 10,076,647 B2 | 9/2018 | Borgos et al. | |
| 2002/0183587 A1 | 12/2002 | Dormer et al. | |
| 2003/0161816 A1 | 8/2003 | Fraser et al. | |
| 2004/0013652 A1 | 1/2004 | Marko et al. | |
| 2005/0025755 A1 | 2/2005 | Hedrick et al. | |
| 2006/0039896 A1 | 2/2006 | Kleinsek et al. | |
| 2006/0045872 A1 | 3/2006 | Miguel et al. | |
| 2006/0122281 A1 | 6/2006 | Escandon et al. | |
| 2006/0129125 A1 | 6/2006 | Copa et al. | |
| 2006/0286137 A1 | 12/2006 | Sandhu et al. | |
| 2008/0217263 A1 | 9/2008 | Higgins et al. | |
| 2008/0267927 A1 | 10/2008 | Lutz et al. | |
| 2008/0286361 A1 | 11/2008 | Dobson et al. | |
| 2009/0082611 A1 | 3/2009 | Levy et al. | |
| 2009/0123366 A1 | 5/2009 | Dobson et al. | |
| 2009/0180965 A1 | 7/2009 | Freyman et al. | |
| 2010/0041944 A1 | 2/2010 | Levy | |
| 2010/0047578 A1 | 2/2010 | Lee et al. | |
| 2010/0069708 A1 | 3/2010 | Tajkarimi et al. | |
| 2010/0087704 A1 | 4/2010 | Berdut-Teruel et al. | |
| 2010/0174137 A1 | 7/2010 | Shim et al. | |
| 2010/0179379 A1 | 7/2010 | Park et al. | |
| 2010/0298816 A1 | 11/2010 | Dobson et al. | |
| 2011/0008299 A1 | 1/2011 | Koullick et al. | |
| 2011/0034753 A1 | 2/2011 | Dobson et al. | |
| 2011/0196187 A1 | 8/2011 | Ludwig et al. | |
| 2011/0213193 A1 | 9/2011 | Nair et al. | |
| 2012/0064448 A1 | 3/2012 | Sakamoto et al. | |

OTHER PUBLICATIONS

Atala, "Future Perspectives in Reconstructive Surgery Using Tissue Engineering", Urologic Clinics of North America, Reconstrcutive Urology, vol. 26, No. 1, Feb. 1999, pp. 157-165.

Bent, et al., "Treatment of Intrinsic Sphincter Deficiency Using Autologous Ear Chondrocytes as a Bulking Agent", Neurology and Urodynamics, vol. 20, 2001, pp. 157-165.

Berjukow, et al., "Membrane Properties of Single Muscle Cells of the Rhabdosphincter of the Male Urethra", The Prostate, vol. 58, 2004, pp. 238-274.

Christ, et al., "Smooth-Muscle Specific Gene Transfer with the Human Maxi-K Channel Improves Erectile Function and Enhances Sexual Behavior in Atherosclerotic Cynomolgus Monkeys", European Urology, vol. 56, Issue 6, Dec. 2009, pp. 1055-1066.

O'Brien, et al., "Restoring Control: The Acticon Neosphincter Artificial Bowel Sphincter in the Treatment of Anal Incontinence", Diseases of the Colon and Rectum, vol. 43, Issue 9, Sep. 2000, pp. 1213-1216.

Oh, et al., "Assessment of biodegradability of polymeric microspheres in vivo: Poly (DL-lactic acid), poly (L-lactic acid) and poly (DL-lactide co-glycolide) microspheres", Arch. Pharm. Res., vol. 16, No. 4, 1993, pp. 312-317.

Schütt, et al., "Biocompatible Magnetic Polymer Carriers for In Vivo Radionuclide Delivery", Artificial Organs, vol. 23, Issue 1, Jan. 1999, pp. 98-103.

Yokoyama, et al., "Persistence and Survival of Autologous Muscle Derived Cells Versus Bovine Collagen as Potential Treatment of Stress Urinary Incontinence", The Journal of Urology, vol. 165, Jan. 2001, pp. 171-276.

U.S. Appl. No. 13/205,039, filed Aug. 8, 2011, Abandoned.
U.S. Appl. No. 15/613,664, filed Jun. 5, 2017, Issued.
U.S. Appl. No. 16/103,390, filed Aug. 14, 2018, Allowed.

* cited by examiner

SYSTEMS AND METHODS FOR THE TREATMENT OF PELVIC DISORDERS INCLUDING MAGNETIC PARTICULATES

CROSS-REFERENCE TO RELATED APPLICATIONS

This application is a Continuation of, and claims priority to, U.S. application Ser. No. 16/103,390, filed on Aug. 14, 2018, entitled "SYSTEMS AND METHODS FOR THE TREATMENT OF PELVIC DISORDERS INCLUDING MAGNETIC PARTICULATES", now U.S. Pat. No. 11,007,357, which is a Continuation of U.S. application Ser. No. 15/613,664, filed on Jun. 5, 2017, now U.S. Pat. No. 10,076,647, which is a Continuation of U.S. application Ser. No. 13/205,039, filed on Aug. 8, 2011, now U.S. Pat. No. 9,669,200, which claims priority to U.S. Application No. 61/371,232, filed on Aug. 6, 2010, and U.S. Application No. 61/371,609, filed on Aug. 6, 2010, the disclosures of which are incorporated by reference herein in their entirety.

FIELD OF THE INVENTION

The present invention relates generally to targeted treatment delivery and, more particularly, to targeted introduction, positioning and control of cells, drugs or other agents treating various pelvic health issues or disorders.

BACKGROUND OF THE INVENTION

Erectile dysfunction (ED) is believed to affect more than ninety million men in the United States and Europe, with seventeen million presenting with severe conditions that greatly interfere with the ability to initiate and maintain erections. ED may arise from a number of causes. Age brings on a lack of arterial elasticity in vessels supplying blood to erectile tissues. Damage to nerves necessary for initiating and sustaining erections brought on by chronic conditions (such as diabetes) or by injury can lead to dysfunction. A significant cause of nerve damage comes from injury that occurs during prostate surgeries, especially radical prostatectomies. Although new surgical procedures have been introduced that conserve the nerves in this region, a majority of men who undergo such procedures can still expect some degree of post operative ED.

A number of oral medications for treating ED have entered the marketplace in recent years, including VIAGRA, CIALIS and LEVITRA. These medications all provide significant relief to a large segment of men with ED. However, they each require that the medication be taken in advance of initiation of sexual activity and their effects may be delayed if ingested with food. Further, the effectiveness of such drugs can vary greatly from patient to patient, and is even ineffective in a large cross-section of patients.

Various treatments have also been tried in connection with ED, including administration of Prostaglandin E1 by injection into the cavernosum of the penis, by administration of a suppository into the urethra and by topical administration. These approaches allow for less advance preparation, but are neither consistently effective nor desirable applications across patient populations, especially radical prostatectomy patients.

Surgical interventions are also available for addressing ED, especially where medications are ineffective or contraindicated. Penile implants of many different configurations are used to provide support for an erection. These implants are effective in restoring patient sexual satisfaction. Increasingly, these implants have been engineered to be completely concealed within the patient. However, implants may fail over time and replacement or total removal may be required potentially leaving the patient with no relief at all. In addition, penile implants are an end stage treatment, and it is often desirable to provide treatment earlier in the disease state. Thus, there is a desire to obtain a minimally invasive yet effective and durable solution to treat ED that can be used with minimal to no side effects.

In addition to ED, there is a need for alternative yet effective solutions to treat other damaged or defective tissues within the pelvic region of a patient (male or female), including conditions such as male and female fecal and urinary incontinence, bladder pain, vaginal prolapse, and overall uterine health.

SUMMARY OF THE INVENTION

Various embodiments of the present invention can be utilized to localize or deliver cells, biologics and/or drugs to a specific target area to treat pelvic health disorders. The delivery mechanism can be directed to cells associated with magnetic particulates, or magnetic particulates such as magnetic microparticles (MMPs) coated with biologics or drugs, that are adapted to treat a pelvic disorders or conditions.

Treatment applications can include ED, urinary and fecal incontinence, prolapse, fistulas, fibroids, abnormal uterine bleeding, prostatic hyperplasia, cancer, and the like.

One embodiment of the invention provides a system for the treatment of a pelvic disorder. The system includes magnetic particulates which are either (i) physically associated with a cell population (ii) or physically associated with a biologic or drug, or both (i) and (ii), which are configured for injection into a pelvic tissue. The system also includes a device configured for placement on or into, or configured to be associated with, a pelvic anatomical structure selected from the group consisting of the urethra, the penis, the vagina, and the rectum. The device comprises a member capable of providing a magnetic field which influences the positioning of the magnetic particulates within the pelvic tissue.

In exemplary embodiments, the magnetic-field generating device is associated with permanent magnets and/or electromagnets, and the device is configured for used on or in the urethra, the penis, the vagina, or the rectum.

A related embodiment of the invention provides a method for the treatment of a pelvic disorder. The method comprises a step of delivering a treatment composition to pelvic tissue, wherein the composition comprises magnetic particulates, and in the composition the magnetic particulates are either (i) physically associated with a cell population (ii) or physically associated with a biologic or drug, or both (i) and (ii). The method also comprises a step of placing a device in proximity to tissue where magnetic particulates are delivered or intended to be delivered, wherein the device is configured for placement on or into, or configured to be associated with, a pelvic anatomical structure selected from the group consisting of the urethra, the penis, the vagina, and the rectum, wherein the device comprises a member that provides a magnetic field and affects positioning of the magnetic particulates within the pelvic tissue.

The system and method of the invention can further include an injection device capable of injecting the cell population comprising the magnetic particulates or a biologic or drug associated with the magnetic particulates into pelvic tissue.

Other embodiments of the invention that are directed to the treatment of ED in male patients can include a penis lifter and mixer system having an external device configured to manipulate the penis and move cells, biologics, or drugs within the vascular spaces to tissue in need of regeneration. For instance, the device can include a construction band placed in or on the penis to provide a gentle but effective rotational force on the dorsal surface of the penis to allow a cell solution to move through the tissue from base to tip and back again in a controlled manner. This will, in turn, allow the cell solution to fill all of the spaces to give the cells an opportunity to take hold of the local tissue to advance regenerative opportunities.

DETAILED DESCRIPTION

Figure 1:
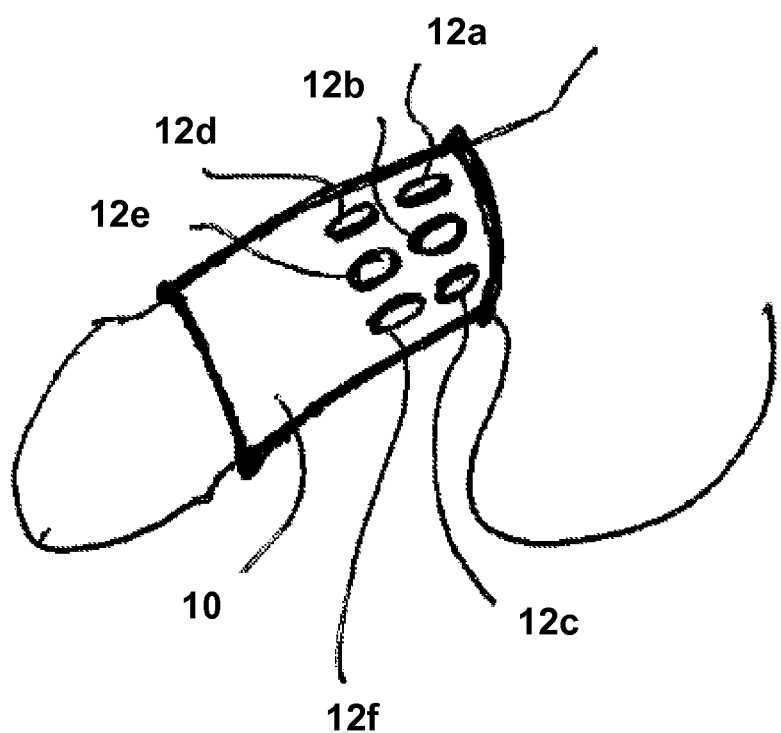
FIG. 1 is a schematic illustration of a condom on a penis with permanent magnets attached to the condom around its circumference.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Various embodiments of a localized agent or cell delivery system and methods are provided. A variety or combination of cells, biologics and/or drugs can be delivered to specific target areas of tissue regions to treat disorders such as ED, urinary and fecal incontinence, bladder pain, vaginal prolapse, fistulas, fibroids, uterine bleeding, cancer and other pelvic health issues. The cells, biologics and/or drugs are associated with magnetic particulates. A part of the system and method is a device that provides a magnetic field which influences the positioning of the magnetic particulates and associated cells, biologics, or drugs within the pelvic tissue. The systems can optionally include other devices adapted to facilitate the delivery or introduction of the cells, biologics and/or drugs, such as injection devices or devices that mechanically promote the distribution of the cells, biologics and/or drugs in the tissue. These devices can be constructed of materials such as polymers, metals, and other like materials compatible for use in treating the disclosed and contemplated pelvic disorders or conditions.

Magnetic particulates can be associated with the cells, biologics and/or drugs so that when delivered to a target tissue in the body and affected by the magnetic field, the magnetic particulates direct positioning of the injected material within the tissue. Magnetic particulates can be associated by a physical or chemical association between the magnetic particulates and the cells, biologics and/or drugs, or by placing the magnetic particulates, for example, within cells.

As used herein, "magnetic particulates" include any type of spherical or non-spherical (irregular shaped) particle made of or including magnetic material. Magnetic material suitable for use in the body includes magnetic iron oxides like $Fe_3O_4$ (magnetite) and $\gamma$-$Fe_2O_3$ (maghemite) The magnetic particulates associated with the cells, biologics and/or drugs are considered "biocompatible" as they can be used in the body without presenting toxicity concerns or eliciting a negative cellular response. Iron oxide particulates have been used in the body and can be excreted via the liver.

Magnetic particulates can be described by geometric as well magnetic properties, if desired. Geometric parameters include, for example, size, shape, bond lengths, composition, and crystal structure, whereas magnetic parameters include, for example, magnetic moments, saturation magnetization, and remnant magnetization. Techniques such as x-ray diffraction (XRD) and transmission electron microscopy can be used for geometric characterization, and magnetometry can be used for magnetic characterization of the magnetic particulates.

Magnetic particulates include nanoparticles and microparticles having magnetic properties. For purposes of discussion relating to size, magnetic nanoparticles have a size of 999 nm or less, such as in the range of about 10 nm to about 500 nm. Magnetic microparticles are characterized as having a size of 1 µm or greater, such as in the range of 1 µm to about 100 or 1 µm to about 20 µm.

In some cases, magnetic particulates are prepared predominantly (e.g., >95%) or entirely from magnetic material, such as magnetic iron oxides. These preparations are typically in the nanoparticulate size range. Various techniques are available for the synthesis of magnetic nanoparticles including: reduction of metal-salts, gas-phase reduction of metal complexes, micro-emulsion, and thermal decomposition of metal-carbonyl complexes. Synthesis techniques can include use of surfactants to control particle size, as well as use of acidic material such as citric acid or oleic acid to stabilize the particles. Particles can be coated, such as with a polymer or a surfactant to prevent aggregation of the magnetic particulates. Exemplary materials that prevent particle aggregation or precipitation are dextran and carboxydextran. Magnetic nanoparticulates are available from, for example, Sigma-Aldrich, as well as those sold under the tradename Ferucarbotran™ (Resovist™; Bayer Schering Pharma AG, Germany). Magnetic nanoparticles can be incorporated into larger structures, such as cells, microvessicles, or microparticles, or can be directly associated with drags or biologics.

Some embodiments of the invention utilize magnetic microparticulates, and in some preparations the magnetic material may represent a portion of the overall material of the microparticle, with the remaining portion being a non-magnetic material, such as a polymeric material, a drug, or biologic, or combinations thereof. However, the presence of the magnetic material in the particle still provides the microparticle with magnetic properties.

In some aspects, the system and methods utilize magnetic polymeric microparticles. Polymers suitable for polymeric microparticles include biocompatible non-degradable or degradable polymers. Exemplary biodegradable polymers include natural polymers such as starch, dextran, and albumin, and synthetic degradable polymers such as polyesters, like polylactide and polyglycolide, and polyamides.

Magnetic polymeric microparticles may be prepared by incorporating magnetic oxides into polymeric spheres. Polymeric spheres can be prepared with magnetic nanoparticles entrapped or impregnated in the sphere (for example, see, Oh, II., et al. (1993) Arch. Pharm. Res. 16:312-317). Entrapment methods can produce particles with a magnetic core composed of dispersed nanoparticle clusters (5-50 nm per particle) or nanoparticles surrounded by a polymer matrix. Magnetic nanoparticles can be suspended in the polymeric solution prior to cross-linking or solvent evaporation. The impregnation method involves the incorporation of magnetic oxide particles within the pores of preformed microspheres with a homogenous precipitate of magnetic oxide particles within the whole particle (for example, see, Schutt, et al. (1999) Artificial Organs 23:98-103).

In some aspects, a drug or biologic is used in the microparticle preparation process and incorporated into the microparticle along with the magnetic particulates.

Some embodiments of the invention utilize magnetic particulates having surface chemistries useful for interaction with a target moiety, such as a drug, a biologic, or a cell. In some cases, these types of magnetic particulates are coated with a material, such as a polymer, or made from a polymeric material, that provides a chemistry on the particulate surface that is useful for bonding or association with a target moiety. For example, magnetic polymeric microparticles can coated with oligomeric compounds, forming a thin shell to which specific ligands can be linked. Some biologics, like antibodies, can be directly adsorbed on the particle surface as a result of hydrophobic interactions, or they can be covalently coupled by first activating a chemical group on the surface of the particle. Surface functionalized magnetic microparticles can further be associated with a drug, cell, or biologic through chemical reaction or interaction between the surface chemistry on the microparticles and a portion of the drug, cell, or biologic. Exemplary surface chemistries include, but are not limited to, carboxyl, streptavidin, and coordination complexes that allow for multivalent binding with a suitable target moiety. Magnetic polymeric microparticles having surface chemistries suitable for bonding to various drugs, biologics, and cells are commercially available from, for example, Bangs Laboratories (Fishers, Ind.).

Alternatively, drugs or biologics useful for treatment pelvic tissue conditions can be incorporated into a microcapsule along with magnetic nanoparticles. An exemplary preparation is an albumin microcapsules (0.2-2.0 μm) containing both $Fe_3O_4$ particles (10-20 nm) and chemotherapeutic agents (for example, see, Arshady, et al. (1990) Journal of Controlled Release 14:111-131).

In some embodiments, the magnetic particulate is associated with a drug that is useful for the prevention or treatment of a condition Classes of drugs for treatment of pelvic tissue related conditions include but are not limited to: analgesics, anesthetics, antibiotics, anti-cancer substances, anti-cholinergics, anti-coagulants, anti-inflammatory agents (such as NSAIDs), anti metabolites, antimitotics, antioxidizing agents, antiproliferatives, including antiangiogenesis agents, antiseptics, antiviral agents, cell response modifiers, chemotherapeutic agents, extracellular matrix components, growth hormone antagonists, immunosuppressive agents, muscle contractants, polynucleotides and derivatives thereof, opioids, prostaglandins, steroids, thrombolytic agents, vasodilators, and vasospasm inhibitors.

Drugs that can be associated with the magnetic particulate and useful for the treatment of erectile dysfunction include phosphodiesterase type 5 inhibors, such as sildenafil, avanafil, lodenafil, mirodenafil, tadalafil, and varendenafil; prostaglandin $E_1$. (PGE1; alprostadil); papaverine; and phentolamine. Biologics that can be associated with the magnetic particulate and useful for the treatment of erectile dysfunction include gene therapy agents, such as nucleic acids encoding for potassium channel proteins, such as the large conductance, calcium channel protein Maxi-K (Slo) (Christ et al. (2009) European Urology 56: 1055-1066).

Drugs for proposed treatment of urinary incontinence include tachykinin-receptor (NK) antagonist TAK637 (NK-1 receptor antagonist); oxybutynin; and resiniferitoxin A drug useful for the treatment of fistula (in women with Crohn's disease) is infliximab (Remicade).

Chemotherapeutic drugs for the treatment of malignant growths, such as prostate cancer, include vinblastine, mitoxantrone, cisplatin, methotrexate, carboplatin, etoposide, mitomycin-C, 5-fluorouracil, vincristine, bleomycin and ifosfamide.

After the treatment composition has been injected into pelvic tissue and the drug has been positioned as desired via use of the magnetic field generating device, the drug can be become unassociated with the magnetic particulate to provide a pharmacological effect.

In some aspects of the invention cells that are associated with magnetic particulates are used for treatment. The magnetic particulates can be associated with the cell by incorporating the particulate into the cell, such as by endocytosis, or by binding particulates to the outer surface of the cell, such as through a membrane protein interaction. Cell-based therapies can be useful for the reconstruction or regeneration of damaged or dysfunctional pelvic tissue.

In some aspects, a cell population that includes primary cells or stem cells is obtained from adipose tissue and associated with the magnetic particulates for the treatment of a pelvic condition. Stem cells can be obtained from a patient using procedures such as surgical or suction lipectomy. Cells obtained by lipectomy can be associated with the magnetic particulates and then reintroduced into the same patient, thereby providing an autologous source of cells. Adipose tissue can be processed to separate the adipose-derived stem cells from the other material including other cellular and non-cellular material in the adipose tissue. Preparation methods can include steps of washing the tissue, treating the tissue with collagenase or trypsin, or optionally with mechanical agitation. Liposomes, which are generally aggregated, can be separated from free stromal cells which include the stem cells and other cells such as red blood cells endothelial cells, and fibroblast cells, by centrifugation. Erythrocytes can be lysed from the suspended pellet and the remaining cells can be filtered or centrifuged. Optionally, cells may be separated by cell sorting or separated immunohistochemically. Methods for the preparation of adipose-derived stem cells are described in commonly assigned application number. WO 2009/120879.

Prior to use in the system or methods of the invention, stem cells may optionally be cultured and, if desired, assayed for number and viability to assess the yield.

Various techniques can be used to incorporate magnetic nanoparticles into cells, such as by nanomagnetic transfection, specific targeting and endocytosis of nanoparticles through the use of transferrin receptors, magnetodendrimers, or by electroporation.

For nanomagnetic transfection a magnetic force is applied beneath the cells to be transfected. This draws the magnetic nanoparticle onto cells on the bottom of the multi-well plate or cell culture flask used. The magnetic particulate is delivered into, target cells, generally via endocytosis. This leads to rapid and efficient transfection without disturbing membrane architecture and without causing chromosomal damage or leaving holes in cell membranes. (see, for example, Dobson, J., et al. (2008) Eur. Cells & Mater. 16: 48).

Surface coated magnetic nanoparticles, such as carboxydextran, poly-L-lysine, D-mannose, or poly(N,N-dimethylacrylamide) may be attached to the outer surface of cells. Ferucarbotran™ is a commercially available preparation of carboxydextran-coated super paramagnetic iron oxide particles.

Optionally, a composition including magnetic particulate-associated cells can include material that promotes cell survival and/or integration into the tissue in which it has been injected into. The material can be a natural material that serves as a cellular scaffolding or extracellular matrix material.

In some aspects, a composition with cells can be mixed with mechanically processed adipose tissue. To obtain this material, lipoaspirate from a patient can be obtained and then disaggregated by mechanical force, such as by cutting, chopping, or mincing the adipose tissue. Collagenase or trypsin (enzymatic) digestion is not performed to maintain the scaffolding features of the adipose tissue. In some preparations, the cells are mixed with the undigested portion of the adipose tissue at a weight ratio in the range of about 1:1 to about 1:4. Methods for the preparation of an adipose tissue-derived scaffolding for cells are described in commonly assigned International Application PCT/US2009/038426 (WO2009/120879).

In some embodiments, the treatment composition including magnetic particulate-associated cells further includes Platelet Rich Plasma (PRP). PRP is blood plasma enriched with platelets. Through degranulation of the platelets, PRP can release different cytokines that can stimulate healing of soft tissue. Processes for PRP preparation include the collection of centrifugation of whole blood which separates PRP from platelet-poor plasma and red blood cells. In some cases, the adipose-derived stem cells are combined with PRP cell based therapy. The healing proteins in PRP are advantageous and can assist in making the sinusoid spaces within the cavernosum of the penis "sticky" for the attraction and retention of the treatment cells. PRP also includes many regenerative proteins to hasten healing. Leveraging the grasping capability of PRP following an injection of adipose derived cells serves as an optimal combination to provide not only duplicitous sources of regenerative proteins and cytokines to improve healing, but also offers facilitates tissue adherence. The adhesive or retention function of the PRP will assist in preventing the cells from migrating or being lost through vascular flow to the lungs. This improved cell retention within the cavernosum provides and signals vascular regeneration to treat erectile function.

In some embodiments, the treatment composition including magnetic particulate-associated cells further includes Platelet Poor Plasma (PPP). PPP is typically characterized by a very low number or platelets (<50000/uL) and a high concentration of fibrinogen. PPP can be prepared in a centrifugation process that separates it from PRP and red blood cells. PPP can provide an autologous scaffold-like material to keep injected cells local to the injection region to improve the regenerative potential of the cells. PPP can be beneficial to tissue as well. The PPP can include a porous gelatinous material to keep cells local to the injection site, allowing the cells to stay local and thereby better impact the intended target tissue. PPP can allow the movement of cytokines and other signaling molecules in and out of the tissue for regenerative mechanisms local to the injection site. The PPP and cell devices can be combined into one delivery tool.

As used herein, a "therapeutic composition" includes the magnetic particulates associated with cells, biologics, or drugs, or combinations thereof. The composition can contain a therapeutically effective amount of cells, biologics, or drugs suitable when used in conjunction with the methods of the invention. A therapeutically effective amount refers to that amount of cells, biologics, or drugs alone, or optionally together with other substances, that produces the desired effect (such as treatment of a medical condition such as erectile dysfunction, or tissue repair for the treatment of weakened pelvic anatomy) in a patient. During treatment, the amounts of cells, biologics, or drugs used will depend upon such factors as the particular condition being treated, the severity of the condition, the individual patient parameters including age, physical condition, size and weight, the duration of the treatment, and any optional concurrent therapy, as recommended by the health practitioner. A physician or veterinarian of ordinary skill can readily determine and prescribe the effective amount of cells, biologics, or drugs required to affect the condition.

The therapeutic composition can include one or more excipients that improve the stability of the composition, and/or enhance the activity of the biological, drug, or cellular active in the composition. Additional excipients can include additives or auxiliary substances such as an antioxidants, antiseptics, isotonic agents, and buffering agents.

A "subject" refers to an organism to which the system and methods of the invention can be applied. The subject can be a human (male or female), another mammal having pelvic anatomy appropriate for application of the system and methods of the invention. For example, the subject can be a domesticated mammal such as a dog, cat, horse, cow, sheep, rabbit, etc.

Optionally, the system can include an injection device capable of injecting a therapeutic composition into pelvic tissue. Exemplary injection devices include needles, syringes, trocars, cannulas, catheters, tubes, and other devices having delivery capabilities. An injection device configured for delivery of the therapeutic composition in a subcutaneous, intramuscular, periurethral, or intraperitoneal manner can be used.

Treatment can involve a single injection, or multiple injections of treatment composition. If multiple injections are performed, the injections can be performed at the same injection site, or at different sites in the general area of treatment (e.g., multiple sites along the surface of the penis.) One mode of injection involves advancing a needle into tissue from an area outside the body. Another mode of injection involves use of a device which is placed within the body, such as a catheter, and then from that device a needle pierces a tissue in the body and the composition is delivered into the desired tissue location.

For example, with regards to the penis, in one mode of practice, needle injection of the therapeutic composition from outside the body can be made through the skin of the penis and the superficial and deep facia, and into target tissue such as the corpus cavernosum or the corpus spongiosum. In another mode of practice, needle injection of the therapeutic composition from inside the body can be made using a urethral catheter having a needle which extends from the catheter and pierces the urethral wall and into the corpus cavernosum or the corpus spongiosum, or into the prostrate.

In some aspects, the system and methods include an injection device that is capable of delivering the treatment composition transurethrally into a desired target tissue. For transurethral injection, the target tissue may be selected from corpus cavernosum, bladder, and prostrate.

One device that can be used for transurethral delivery of a therapeutic composition is a needless injector device. The device has a shaft that can be navigated through the urethra, to place the distal end of the device at a target location where the injection is desired. The device can eject fluid from at least one injection orifice located at the distal end of the shaft. Optionally, multiple injection orifices may be located at one or more locations along a length of or about a circumference of a shaft distal end. The fluid-based composition penetrates through a surface of a tissue, without the use of a needle, and into the bulk of the tissue, and dispersing as particles or droplets within the tissue below the tissue surface. A needleless transurethral delivery device which can be used as a component in the system and methods of the invention is described in commonly assigned U.S. Publication Number 2006/0129125 (Copa et al.).

Another device that can be used for transurethral delivery of a therapeutic composition is a needled injector device. The needled device also has a shaft that can be navigated through the urethra, to place the distal end of the device at a target location where the injection is desired, but the device can eject fluid from a needle located near the distal end of the shaft. A needled transurethral delivery device which can be used as a component in the system and methods of the invention is described in commonly assigned U.S. Publication Number 2006/0122281 (Sousa Escandon et al.).

The system also includes a device that provides or generates a magnetic-field ("magnetic-field device"). The magnetic-field device can be configured for placement on or into a pelvic anatomical structure such as the urethra, the penis, the vagina, and the rectum. Alternatively, the device can be configured to be associated with a pelvic anatomical structure as described. In exemplary aspects, the magnetic-field device can be in the form of a male condom, a penis ring, an intravaginal device, a pessary, or a urethral catheter.

When placed on or into the anatomical structure in the pelvic area, the magnetic-field device can influence the positioning of the magnetic particulates within the pelvic tissue. The magnetic design parameters in the magnetic-field device can be tailored to conform to a particular treatment protocol. The magnetic-field device can be useful for maintaining the cells, biologics, or drugs at the desired treatment area so they are not removed by fluidics of the vascular or lymphatics system in the treatment area.

In some modes of practice, the magnetic-field device can produce the guided migration of cells, biologics and/or drugs associated with the magnetic particulates. Cells, biologics and/or drugs associated with the magnetic particulates can be acted on by magnetic fields and gradients generated by the devices of the invention in order to produce the desired motion. Magnetic fields and gradients are used to produce forces and torques on of the magnetic particulates inside the pelvic tissue. Through control of the fields and gradients, the magnetic particulates can be made to move through the pelvic tissue thereby carrying the cells, biologics and/or drugs with them.

As a general matter, the magnetic field generating device is associated with one or more series of permanent magnets, or one or more electromagnets. The magnet devices can include coils, magnetic nodes, sleeves, inductors, solenoids, and other like structures or components to facilitate the positioning of the magnetic particulates with associated cells, biologics, or drugs within the pelvic tissue.

Permanent magnets can be made of materials such as alnico, neodymium iron boron (NdFeB), and samarium cobalt (SmCo). Small permanent magnets, including those having dimensions less than a millimeter, are commercially available (e.g., BM Magnetics, Leominster, MA) Permanent magnets can be associated with the devices of the systems in a variety of ways. For example, permanent magnets can be adhered to a portion of the device using an adhesive, can be incorporated into a plastic material of the device by using the magnets along in an extrusion, lamination, or molding process; can be sintered or welded to a portion of the device, can be mechanically fastened to the device, or can be shaped to fit or interlock with a portion of the device.

In some aspects, the device includes an electromagnet, which is a non-permanent magnet in which the magnetic field is produced by the flow of an electric current conductive material, such as a coil. A current flowing through the coil material produces a magnetic field, and the field disappears when the current ceases. In the presence of a current, magnetic domains align with the applied field, causing an increase in the magnetic field strength. One or more electromagnets associated with the device can be controlled in a variety of ways to provide a magnetic field that influences positioning of the magnetic particulate-associated cells, biologics, or drugs in the pelvic tissue for a particular condition to be treated. For example, the magnetic field can be rapidly manipulated over a wide range of values by controlling the strength of the electric current, thereby controlling the forces acting on the particulates. The duration of an applied magnetic field can also be controlled, thereby controlling the amount of time forces act on the particulates. Further, in some embodiments, when more than one electromagnet is used with a device, the device can have an electronic control to provide magnetic fields at different locations on the device at different times. A method using this type of control can cause the movement of particles in different directions at different times to enhance penetration and distribution of the cells, biologics, or drugs throughout the tissue to be treated. It can also cause the particles to be maintained within the tissues in which they were injected rather than being carried off by fluidics of the body. In addition, the invention also contemplates use of electromagnets formed by including a permanent magnet in an electronic circuit. In these arrangements, a magnetic field is present until a current is applied.

In some aspects of the invention, the magnetic particulates with associated cells, biologics, or drugs can be retained within the penis with the use of a proximate or external magnet device. The magnetic device can be implemented in various configurations to promote the desired and proximate magnetic field interaction with the magnetic particulates with associated cells, biologics, or drugs. In some modes of practice the magnetic field generating device is used for the controlled retention and migration prevention. Through use of the device, injected magnetic particulates with associated cells, biologics, or drugs are better positioned and retained at the site of the damage or disorder.

In one aspect, the system and methods of the invention include a magnetic-field device used in conjunction with the penis. To position and maintain the external magnets proximate to the magnetic particulates with associated cells, biologics, or drugs, the magnets can be provided with a cuff, a condom-like device, or other like devices adapted to engage or surround at least a portion of the penis. Exemplary devices include magnetic condoms and magnetic penis rings, or other like devices adapted to engage or surround at least a portion of the penis. One embodiment of the invention uses a condom that includes a permanent magnetic material associated with the condom. The condom can formed of flexible polymeric sheath material and can have one or more permanent magnet(s) associated with the polymeric sheath material. Polymeric sheath materials can be selected from those typically used to make condoms, such as, polyvinyl chloride (PVC) or latex. The one or more magnets can be associated with the sheath at one or more points along the sheath length. Since the sheath can be rotated on the penis during a step of treatment, the positioning of the magnet(s) with regard to the circumference of the sheath may not be critical for some embodiments.

In one embodiment as shown in FIG. 1, the partial condom 10 has a series of permanent magnets (12a, 12b, 12c, 12d, 12e, 12f, etc.) arranged around the circumference of the condom. The magnets can be placed around the circumference along the entire length of the condom, or can be placed at positions near the proximal end, distal end, or the center, or combinations thereof, along the length of the condom. FIG. 1 shows the magnets being placed near the proximal end of the condom. The number and size of the permanent magnets can be chosen based on the desired strength of the magnetic field to be associated with the condom. Exemplary designs include a series of magnets arranged around the circumference at any particular location along the condom length. To construct the magnetic condom, an adhesive can be used to glue the permanent magnets to the latex sheath. The partial condom shown in FIG. 1 has an open distal end, but can be provided with a closed distal end to cover the glans penis, similar to traditional condoms.

Figure 2:
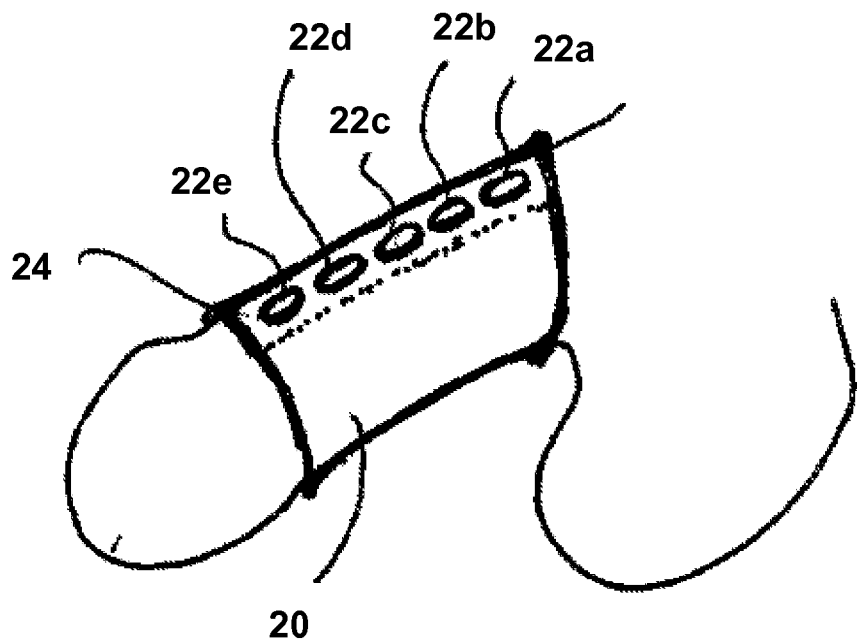
FIG. 2 is a schematic illustration of a condom on a penis with permanent magnets attached to the condom on a strip along the condom length.
Figure 3:
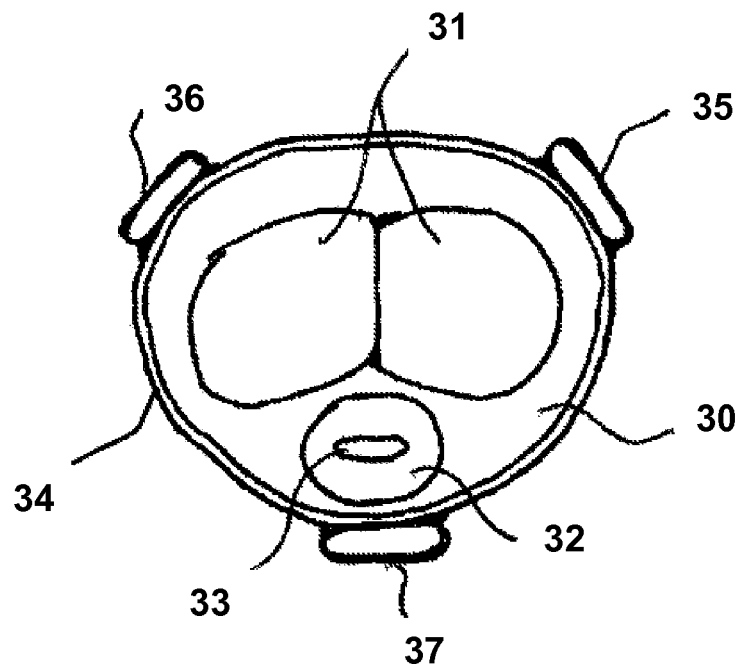
FIG. 3 is a schematic illustration of a cross section of a penis with condom showing the location of magnets equally spaced around the circumference of the condom.
Figure 4:
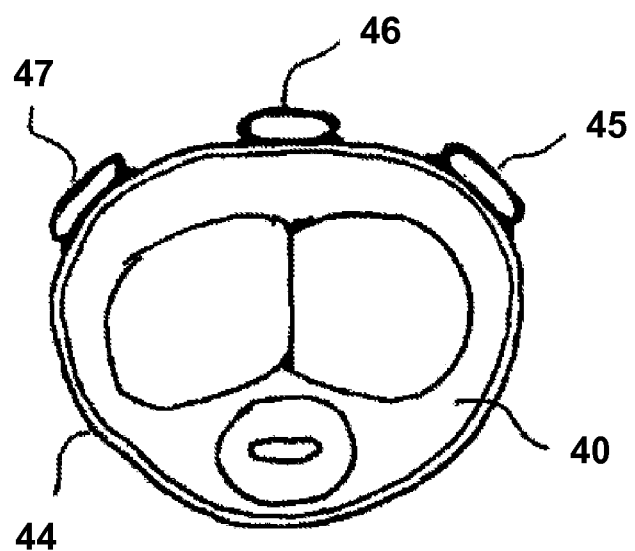
FIG. 4 is a schematic illustration of a cross section of a penis with condom showing the location of magnets unequally spaced around the circumference of the condom.

Another embodiment, shown in FIG. 2, uses a series of permanent magnets arranged along the length of the sheath. For example, magnetic condom 20 includes a series of permanent magnets (22a, 22b, 22c, 22d, 22e, etc.) that are associated with the sheath in a linear configuration (running along strip 24) from the proximal to distal end of the sheath. In other embodiments, the magnetic condom has more than one strip of magnets located around its circumference. For example, the magnetic condom can include two, three, four, or more than four strips of magnets around its circumference, each strips spaced equally around the circumference, or not spaced equally around the circumference. For example, FIG. 3 is a cross-sectional view of the penis 30 (showing anatomical structures of the corpus cavernosum 31, corpus spongiosum 32, and urethra 33) with condom 34 having three strips of magnets (35, 36, and 37) spaced equally around the circumference of the condom. In another embodiment, FIG. 4 is a cross-sectional view of the penis 40 and condom 44 showing three strips of magnets (45, 46, and 47) spaced unequally around the circumference of the condom.

Use of a magnetic condom in conjunction with the methods of the invention are exemplified as follows. A composition that includes magnetic particulate-associated cells, biologics, or drugs can be introduced into the corpus cavernosum by a suitable technique such as needle injection. Injection of the composition can be performed at one or more locations along the length and/or circumference of the penis so that a desired amount of composition becomes present at the tissue sites within the penis. Multiple injections are made into the corpus cavernosum, if desired. In some modes of practice a series of injections may result in a total volume of composition being injected into the penis in the microliter to milliliter range. Injections can be performed prior to placement of the magnetic condom on the penis, or injections can be made after the condom is in place. If injections are made after the condom is in place, the condom can optionally include one or more aperture(s) for the needle to pass through so the sheath does not need to be penetrated with the needle. The one or more apertures may also serve as a guide to for injection sites into the penis.

Figure 5A:
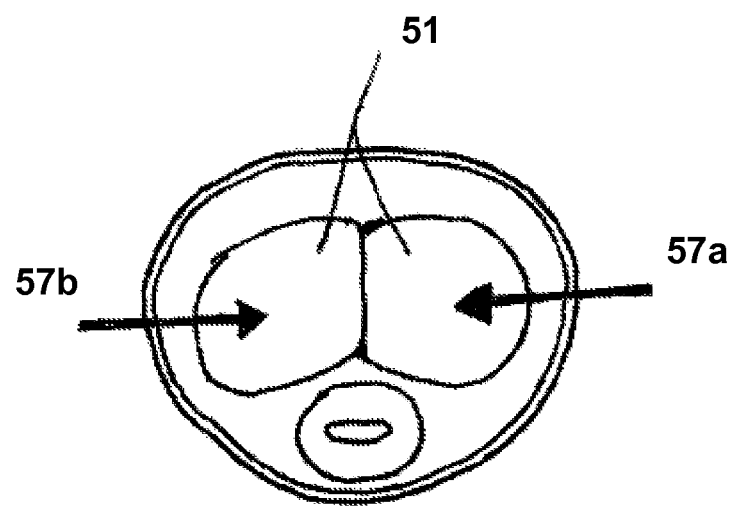
FIG. 5a is a schematic illustration of a cross section of a penis with condom showing the location of injection of a therapeutic composition into the corpus cavernosum.
Figure 5B:
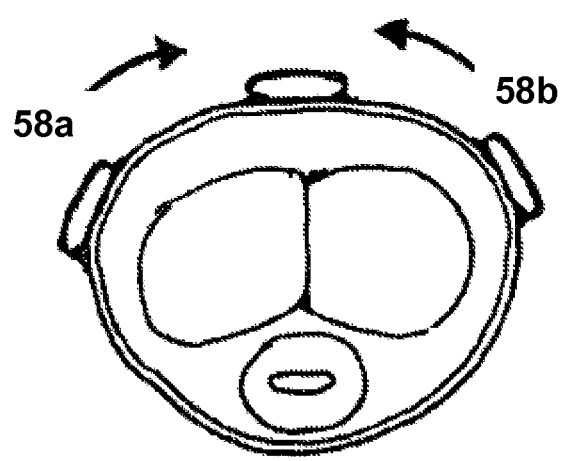
FIG. 5b is a schematic illustration of a cross section of a penis with condom with magnets unequally spaced around the circumference of the condom, with movement of the condom in clockwise and counterclockwise directions.

In some modes of practice, one or more injections of a treatment composition can be made into tissue of the penis adjacent to placement of magnetic strips when the magnetic condom is situated on the penis. For example, with reference to FIG. 5a, arrows 57a and 57b represent injection locations of the composition on the right and left sides of the penis 50, into the corpus cavernosum. The injections can result in a bulk of injected material being present in one or more portions of the corpus cavernosum. When the magnetic condom magnet strip is positioned proximal to the site(s) of injection, the magnetic field can produce forces and torques on the magnetic particulate associated with the cells, biologics and drugs, so that the injected material remains positioned as desired in the corpus cavernosum.

In some modes of practice the magnetic condom is manipulated in a way to enhance distribution and positioning of the injected magnetic particulates with associated cells, biologics, or drugs in the desired tissue location(s) in the penis. For example, the condom can be partially or fully rotated in place on the penis, causing direction of the magnetic field to change. The condom can be rotated clockwise (arrow 58a) and counterclockwise (arrow 58b), moving the magnetic strip over the dorsal side of the penis, from the left to right side, and back from right to left. Optionally, the condom can be moved (e.g., slightly) in a proximal to distal (and reverse) direction as well. This movement of the condom causes changes in the location of the magnetic field and results in the movement of magnetic particulates associated with the cells, biologics or drugs within the corpus cavernosum. This enhances the penetration and distribution of the cells, biologics and drugs into the tissue of the corpus cavernosum, while still positionally maintaining the material in this general area.

In some embodiments, a condom that includes an electromagnet made from a coil of wire is used in the system and the methods of the invention. The coil of wire can be in the form of a tightly wound helix which produces a solenoid effect, and the generated magnetic field affects positioning of the magnetic particulate-associated cells, biologics or drugs in the penis. Exemplary coils that can be attached to the condom have a desired height and diameter for attachment to the condom.

Figure 6:
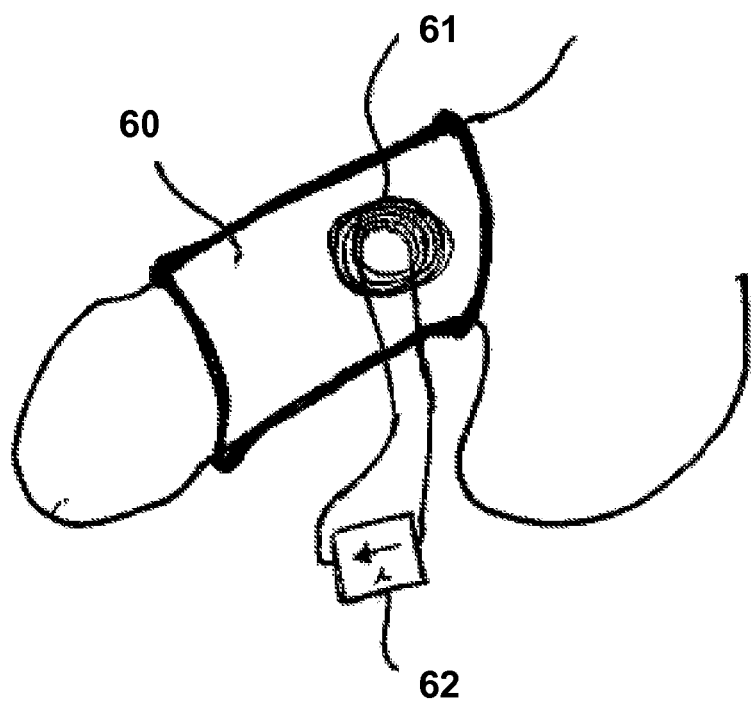
FIG. 6 is a schematic illustration of a condom on a penis with a small electromagnet coil attached to the condom.

Referring to FIG. 6, in another embodiment the condom includes one or more small electromagnetic coils 61 associated with the sheath material of the condom 60. Also shown is a power supply 62, such as a battery pack, that generates the electric current for magnetic field induction from the coil. One or more coils can be associated with the condom in a desired arrangement; for example a condom can include electromagnetic coils around its entire circumference, or a part of the circumference. In some embodiments, the condom can include one or more strips of electromagnetic coils along its length. If the condom includes multiple electromagnetic coils, all of the coils can be in electronic communication with each other so that current passes through all of the coils with a single current. Alternatively, the individual coils, or groups of coils can have separate connections so magnetic fields can be generated at different locations in association with the surface of the condom at different times. For example, in some modes of practice, a magnetic field for one of the coils positioned at a first location on the condom is generated for a first period of time, and subsequently a magnetic field for a second coil is generated for a second period of time, and so forth. The alternating magnetic fields may produce desired positioning of magnetic particulate-associated cells, biologics or drugs within the penis. In some cases, the alternating magnetic fields result in better penetration and distribution of the magnetic particulate-associated cells, biologics or drugs in the corpus cavernosum, while still maintaining this material within this tissue.

Figure 7:
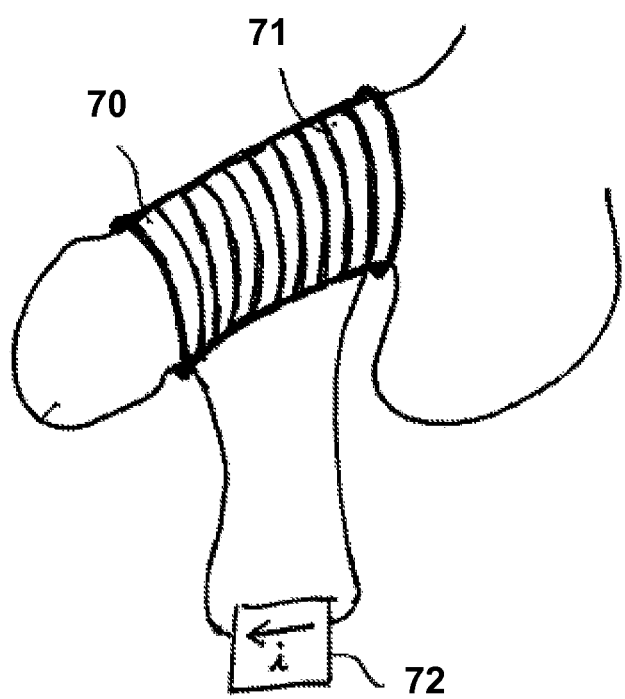
FIG. 7 is a schematic illustration of a condom on a penis with a wire attached to and wrapped helically around the condom to form an electromagnet.

Referring to FIG. 7, in another embodiment the condom 70 includes a wire 71 wrapped around the circumference of the condom 70 in a helical configuration. Also shown is a power supply 72, such as a battery pack, that generates the electric current for magnetic field induction from the coil. The helical configuration can extend for all or a portion of the length of the condom. When an electric current passes through it, the coil generates a magnetic field around the circumference of the penis. The condom can be constructed by wrapping a small gauge wire around the condom using an adhesive to secure the wire to the sheath material. The wire can be wrapped very tightly so there is no spacing between the wire along the helical turns, or can be wrapped so there is a desired amount of spacing (gap) between the wire.

A system that includes the magnetic field-providing condom can optionally include one or more components that would facilitate or enhance use of the system. For example, the system could be provide with a lubricant to facilitate placement of the condom on the penis, or movement of the condom when performing a method of the invention, such as rotating the condom in a clockwise or counterclockwise direction around the penis. A lubricant may be applied to the penis or condom prior to use, or the condom may come pre-coated with a lubricant. The system can also optionally be provided with an agent that prevents or treats bacterial infection, such as an anti-microbial. The anti-microbial may come pre-coated on the condom, or may be a component that is applied prior to or after steps in the treatment process.

Figure 8:
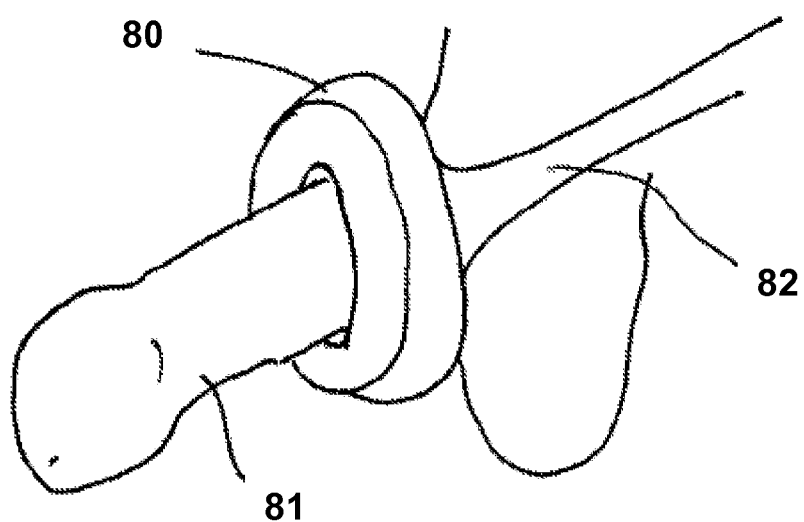
FIG. 8 is a schematic illustration of a magnetic penis ring on a penis.

In another aspect, the system and methods of the invention include a magnetic field-generating penis ring. Referring to FIG. 8, the penis ring 80 can be configured to surround the penis 81 and placed over a portion of its length during use. The ring can include one or more permanent magnets, or an electromagnetic coil, going around all or a portion of the ring. The permanent magnets or electromagnetic coil can be encased within a housing, such as one made from a plastic or rubber material. After the therapeutic composition is injected into one or more desired areas of the penis, the ring can be placed on the penis, or the ring can be placed on the penis prior to injection. In some modes of practice, the ring can be moved along the shaft of the penis, back and forth, to promote desired positioning of the magnetic particulate-associated cells, biologics, or drugs within the tissue. Alternatively, or in combination with the movement along the shaft, the ring can be spun around the penis in clockwise and/or counterclockwise directions. Optionally, the penis ring 80 can be fastened to a belt 82 on opposite sides of the ring, so the ring can be held in place around a patient such as by placing the belt below the patient's waist.

In another aspect, the system and methods of the invention include a magnetic field-generating urethral catheter. The catheter can be adapted for either male or female use. Some urethral catheters are referred to as "Foley catheters," and catheters of these types can be modified to provide a magnetic field for use in the system and methods of the invention. Flexible materials that make the tubing of a urethral catheter are commonly selected from silicone, latex, and polyvinyl chloride (PVC). Normally, a urethral catheter tube is navigated through the urethra so urine can be drained from the bladder from the end of the urinary catheter located within the bladder. Urethral catheters also typically include an inflatable balloon that allows the end of the catheter to be held in the bladder. A modified urethral catheter that provides a magnetic field, and which can be used in the system and methods of the invention, can include one or more permanent magnets, or an electromagnetic coil. Other components, such as a balloon, which is normally used in urine drainage processes, are optional components in the modified catheter. Common sizes of urethral catheters range from 10 French to 28 French (F) (1 F=0.33 mm), with sizes in the range of 12 F-16 F being common for use in adult humans, and having an inner diameter (lumen) in the range of about 1— 3 mm.

A magnetic field-generating urethral catheter can be constructed by loading the inner diameter of the flexible tube of the catheter with one or more permanent magnets, or an electromagnetic coil. The magnets or coil may be present in the inner diameter along the entire length of the tube, or may be present along a portion of the length of the tube, or more than one portion of the length of the tube.

An exemplary method using a magnetic catheter includes one or more injections of a treatment composition into the corpus cavernosum of the penis. When the magnetic field-generating catheter is placed inside the urethra, the magnetic field affects positioning of cells, biologics and drugs, so they are maintained in the desired area for treatment. In some modes of practice, the catheter can be moved back and forth in the urethra to change the location of the magnetic field source, thereby causing movement of the particulates and associated cells, biologic, or drugs in a proximal and distal manner.

A system and method utilizing a magnetic field-generating urinary catheter can be particularly effective for the treatment of patients having undergone radical prostatectomy. For example, a magnetic field-generating urinary catheter can be used in conjunction with magnetic particulates associated with prostaglandin E1 (PGE1), phentolamine, papaverine, Forskolin, or a combination of these drugs.

In some embodiments, the device is in the form of a pessary which associates or incorporates one or more permanent magnets, or an electromagnet, with the structural material used to form the pessary. Pessaries are small medical devices which can be inserted into the vagina or the rectum, and which can be maintained in position at these locations by the pelvic floor musculature. In some modes of practice, a vaginally inserted pessary can be used to treat a condition such as uterine prolapse, stress urinary incontinence, cystocele, or rectocele, while at the same time providing a magnetic field which affects positioning movement of the magnetic particulate-associated cells, biologics, or drugs which have been delivered to the pelvic tissue. Therefore, in some embodiments, the pessary can provide treatment based on the structural support the architecture of the pessary provides, along with the magnetic field action it provides to promote positioning of the injected composition in the target pelvic tissue.

An exemplary system and method includes stem cells associated with magnetic particulates, such as adipose-derived stem cells, and a magnetic-field generating intravaginal or intrarectal pessary. In some modes of practice, the cell-containing composition is injected into a tissue site, such as the levator ani and/or the urethral sphincter for the treatment of stress urinary incontinence (SUI). The adipose-derived stem cells can be promoted to differentiate into smooth muscle cells (SMC) following injection and positioning as affected by the vaginal pessary, for reconstruction of the smooth and skeletal muscles in the defective pelvic floor and for urethral support.

In some modes of practice, magnetic microparticle-associated cells, biologics, or drugs can be placed on a wound healing scaffold and the movement of the cells, biologics, or can be controlled or positionally maintained by one or more magnetic devices.

In some modes of practice, the system and methods of the invention are used to treat a fibroid, such as a uterine fibroid, or a cancerous growth in tissue of the pelvic area. Uterine fibroids are benign tumors that originate from the uterine myometrium (smooth muscle) and the accompanying connective tissue of the uterus. Fibroids include uterine leiomyomas, fibromyomas, and fibromas. For instance, therapeutic compositions can be injected into fibroids, or the uterine artery, and the position of the microparticulate-associated cells, biologics, or drugs can be controlled using a magnetic field providing device, such as a magnetic field-generating pessary. In addition, therapeutic compositions can be injected into the prostate, intravenously, into or around cancerous tumors, or at other desired target sites to facilitate healing and treatment.

In some embodiments, the system and methods of the invention include a device that is used for treating long-term diarrhea or fecal incontinence. Exemplary devices are configured for internal use, such as an artificial anal sphincter (artificial bowel sphincter; O'Brien, P. E., et al. (2000) Dis. Colon. Rectum 43:1213) and those configured for external use, such as an adhesive wafer for application to the anal opening which includes a drainable pouch. Internal or external fecal incontinence devices can include one or more permanent magnets, or an electromagnet, and can be used in conjunction with magnetic particulates associated with cells, biologics, or drugs, for the treatment of fecal incontinence.

Figure 9A:
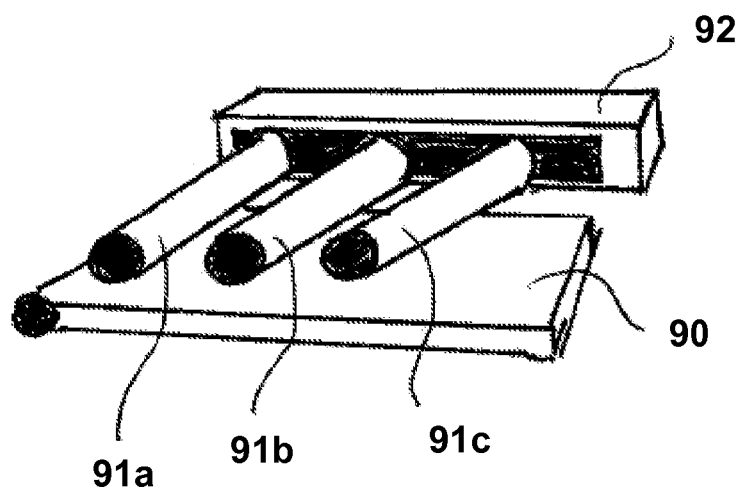
FIG. 9a is a schematic illustration of a penis roller device.

In another embodiment, the invention provides a device that is designed to apply mechanical forces on the penis in order to enhance distribution of a therapeutic composition within tissue of the penis. The device can manipulate the penis to move cells, or other therapeutic material, within the vascular spaces to locate materials of the treatment composition to tissue in need of regeneration. The therapeutic composition can be one that includes the magnetic microparticle-associated cells, biologics, or drugs. With reference to FIG. 9a, the device includes a platform 90 which contacts a surface of the penis, and a series of rollers (91a, 91b, 91c, etc.) arranged perpendicular to the penis when placed on the device, and in a parallel plane as the platform 90. The device may be constructed with just one roller, but multiple rollers (two, three, four, five or more rollers) may be used increase the amount of tissue being manipulated in order to enhance distribution of the therapeutic composition in the penis. The rollers, at one end, can be attached to a roller track 92 which includes a mechanical member such as a chain, rod, or pulley, which drives movement of the rollers.

Figure 9B:
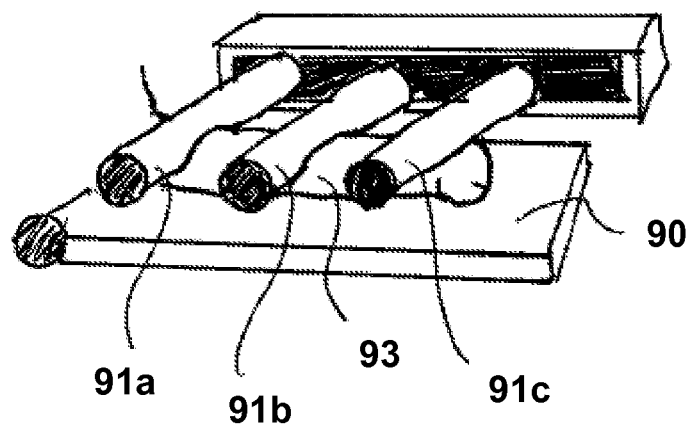
FIG. 9b is a schematic illustration of a penis roller device with penis.

With reference to FIG. 9b, the platform and a roller are arranged in opposition and configured so a penis 93 can positioned between the platform 90 and the rollers 91a, 91b, and 91c. The gap between the surface of the platform and the rollers may be varied based on anatomical considerations, as well as the amount of pressure intended to be exerted on the penis during the treatment method. The rollers can be constructed using a soft material, such as a foam or fabric, that contacts and applies force to a surface of the penis but that preferably avoids causing any tissue trauma. The roller is capable of moving in one or more directions to compress tissue of the penis when it is being moved. In some modes of practice the rollers move back and forth for a distance in the range of less than a centimeter to multiple centimeters. The device can provide a gentle but effective rotational force on the dorsal surface of the penis to allow a therapeutic composition to move through the tissue from base to tip and back again in a controlled manner. This will, in turn, allow the therapeutic composition to fill all of the spaces to give the cells an opportunity to take hold of the local tissue to advance regenerative opportunities.

Figure 9C:
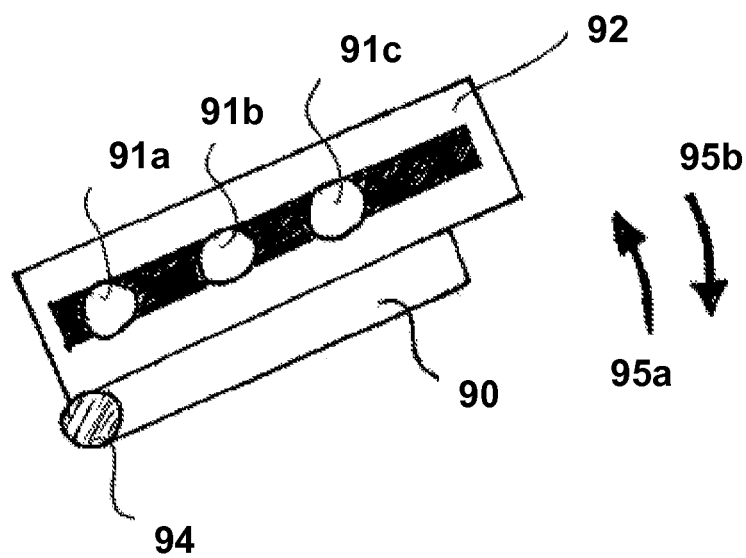
FIG. 9c is a schematic illustration of a penis roller device.

The penis roller device can also function to elevate all or a portion of the penis. By elevating the penis, distribution of the therapeutic material in the penis can be enhanced. According to one arrangement, and with reference to FIG. 9c, the device includes a hinge 94 at the proximal end of the platform 90. The platform can be attached to the roller track 92, and the platform 90 can mechanically pivot on the hinge 94, which elevates the distal end of the platform and the roller track, and elevates the distal end of the penis according to arrow 95a. The platform can then be pivoted back to a horizontal position according to arrow 95b. Elevation of the penis can be performed while the penis is being rolled, or can be performed independently of the penis being rolled.

The penis roller device can also include a magnetic field-generating member that can provide a positioning effect to magnetic particular-associated cells, biologics, or drugs that are injected into the penis. For example, permanent magnets or electromagnets can be included in one or more of the rollers, or the platform. A magnetic field can be provided during the steps of rolling and/or elevating the penis to enhance the distribution and maintenance of particular-associated cells, biologics, or drugs in the penis.

What is claimed is:

1. A system for the treatment of a pelvic disorder comprising:
   (a) a composition comprising magnetic particulates which are either (i) physically associated with a cell population (ii) or physically associated with a drug or a biologic agent, or both (i) and (ii), which are configured for injection into a pelvic tissue; and
   (b) a device configured to be associated with a pelvic anatomical structure, the device having a platform pivotally coupled to a roller and being capable of providing a magnetic field which influences movement of the magnetic particulates and associated cell population, drug, or biologic agent within the pelvic tissue.

2. The system of claim 1 wherein the device includes a wire through which electrical current can flow and which can generate the magnetic field.

3. The system of claim 1 wherein the device includes one or more permanent magnets.

4. The system of claim 1 further comprising an injection device capable of injecting the composition into the pelvic tissue.

5. The system of claim 4 wherein the injection device comprises a syringe configured to inject the composition into a target area of the pelvic tissue.

6. The system of claim 1 wherein the composition comprises stem cells comprising intracellular magnetic nanoparticles.

7. The system of claim 6 wherein the stem cells are adipose tissue-derived stem cells.

8. The system of claim 1 wherein the device is capable of moving in one or more directions to compress bodily tissue when it is being moved.

9. A method for the treatment of a pelvic disorder comprising steps of:
   (a) delivering a treatment composition to pelvic tissue, wherein the composition comprises magnetic particulates, and in the composition the magnetic particulates are either (i) physically associated with a cell population (ii) or physically associated with a drug or a biological agent, or both (i) and (ii); and
   (b) placing a device in proximity to the pelvic tissue where the magnetic particulates are delivered, wherein the device has a platform pivotally coupled to a roller and is capable of providing a magnetic field which influences movement of the magnetic particulates and associated cell population, drug, or biologic agent within the pelvic tissue,
   wherein steps (a) and (b) provide treatment for the pelvic disorder.

10. The method of claim 9, wherein the step of delivering comprises injecting the treatment composition into a tissue in a penis.

11. The method of claim 10, wherein the step of delivering comprises injecting the treatment composition into the corpus cavernosum of the penis.

* * * * *